United States Patent [19]

Lechtken et al.

[11] Patent Number: 4,510,146

[45] Date of Patent: Apr. 9, 1985

[54] GROWTH-PROMOTING FEED AND DRINK

[75] Inventors: Peter Lechtken, Frankenthal; Axel Nüerrenbach, Gruenstadt; Juergen Schole, Wechmark, all of Fed. Rep. of Germany

[73] Assignee: BASF Aktiengesellschaft, Fed. Rep. of Germany

[21] Appl. No.: 376,586

[22] Filed: May 10, 1982

[30] Foreign Application Priority Data

May 15, 1981 [DE] Fed. Rep. of Germany ....... 3119384

[51] Int. Cl.³ ............................................. A61K 31/47
[52] U.S. Cl. ..................................... 514/312; 546/155
[58] Field of Search .......................... 424/258; 546/155

[56] References Cited

U.S. PATENT DOCUMENTS

| 2,189,717 | 2/1940 | Scott | 546/155 |
| 2,986,468 | 5/1981 | Edwards | 424/258 |
| 3,264,305 | 8/1966 | Paquette | 546/155 |

OTHER PUBLICATIONS

Ames et al.-"N"—Oxides of some Hydroxy—and Amino—Quinolines, (1956), 3079–3083.
Chem. Ber., 54 (1921), pp. 1071–1072.
Biochem. J., 63 (1956), pp. 124–130.

Primary Examiner—Frederick E. Waddell

Attorney, Agent, or Firm—Keil & Weinkauf

[57] ABSTRACT

Animal feeds and drinks containing small amounts of compounds of the formula Ia or Ib

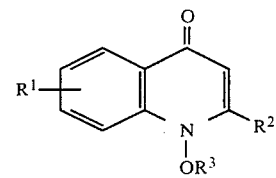

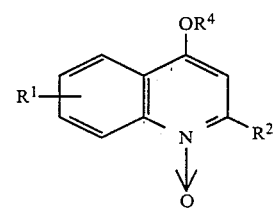

where $R^1$ is hydrogen, low molecular weight alkyl or alkoxy, or halogen, $R^2$ is hydrogen or low molecular weight alkyl and $R^3$ and $R^4$ are hydrogen or a low molecular weight aliphatic or araliphatic radical. The compounds of the formulae Ia and Ib promote growth without exerting an antibiotic action.

3 Claims, No Drawings

GROWTH-PROMOTING FEED AND DRINK

The present invention relates to growth-promoting feeds and drinks, which are virtually free from antibiotic side-effects, for domestic animals and livestock, especially poultry and hogs.

A number of compounds which promote the growth of livestock and/or improve feed utilization are currently in use. The most important examples of these compounds may be found, for instance, in the chapter on "Additives in straight feeds" in the German Feeds Act. The antibiotic or antibacterial effect of these compounds is a significant factor in their performance.

It is an object of the present invention to provide, because of the development of resistance when using the above materials, a growth-promoting or utilization-improving feed which is virtually or completely devoid of an antibiotic or antibacterial action.

We have found that this object is achieved by animal feeds which contain small amounts, ie. from 0.5 to 500 ppm, of compounds of the formula Ia or Ib

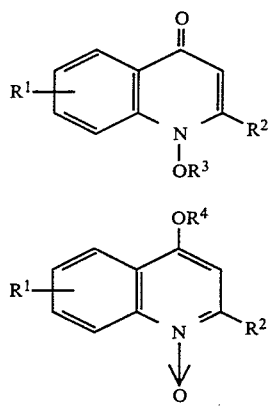

where $R^1$ is hydrogen, low molecular weight alkyl or alkoxy, or halogen, $R^2$ is hydrogen or low molecular weight alkyl and $R^3$ and $R^4$ are hydrogen, a low molecular weight aliphatic radical or an araliphatic radical, preferably methyl, ethyl or benzyl, and that these feeds exhibit a growth-promoting effect on animals, ie. result in a more rapid gain in the weight of the animals and/or improve feed utilization by the animal. At the effective concentration employed, these compounds are devoid of an antibiotic or antibacterial effect.

The compounds of the formulae Ia and Ib can be given to the animals with the conventional feed or, especially in the case of derivatives where $R^3$ or $R^4$ is not H, in the drinking water. Appropriate mixtures can be prepared, for example, from premixes or concentrates (or feed additives) containing from 1 to 50% of compounds of the formula Ia or Ib. The feed premixes, feed concentrates or feeds can be based on any substance of vegetable or animal origin employed for feeding. Advantageous base substances are wheat grits, barley, rye, oat meal, rice bran, wheat bran, soybean meal, corn germ meal, bonemeal, lucerne meal, soybean grits, meat meal, fish meal and mixtures of these.

As assistants, the feed premixes, feed concentrates and feeds may advantageously contain silicon dioxide, wetting agents, antioxidants, starch, dicalcium phosphate, calcium carbonate and/or sorbic acid. The wetting agents may be, for example, non-toxic oils, advantageously soybean oil, corn oil or mineral oil. The various alkylene glycols have also proved advantageous wetting agents. The starch can advantageously be corn starch, wheat starch or potato starch. If desired, the compounds of the formula Ia or Ib can also be applied to carriers, encapsulated in gelatin or micro-encapsulated. These techniques are familiar to a skilled worker.

The optimum amount of active ingredient for any particular species of animal can be introduced by admixture of appropriate amounts of the novel concentrates into the feed mixture specifically intended for that species.

Where $R^3$ or $R^4$ is H, the compounds of the formulae Ia and Ib can be present in a tautomeric equilibrium, namely

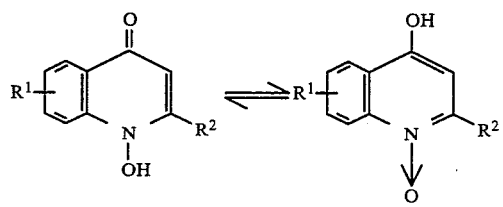

Some of the compounds of the general formulae Ia and Ib have previously been disclosed. Thus, Gabriel and Gerhard (Chem. Ber. 54 (1921), 1071-1072) prepared the compound of the formula II and Cornforth and James (Biochem. J. 63 (1956), 124) prepared the compounds of the formula III.

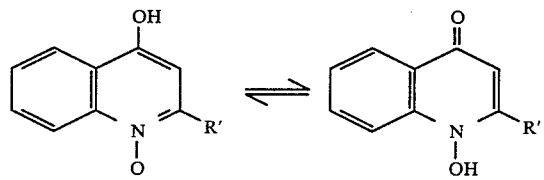

II: R'=CH$_3$

III: R'=C$_7$-C$_{11}$-alkyl

On the other hand, the compounds of the general formulae IVa and IVb

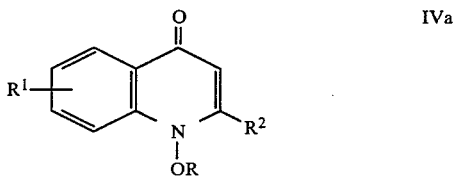

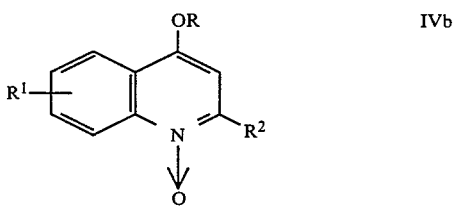

where $R^1$ and $R^2$ have the above meanings and R is methyl, ethyl or benzyl, have not been disclosed previously. These novel compounds are distinguished by a particularly pronounced growth-promoting effect.

The compounds of the formulae Ia and Ib can be prepared, for example, from the correspondingly substituted 4-hydroxy-quinolines of the formula V

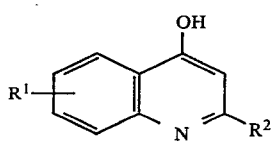

where $R^1$ and $R^2$ have the above meanings. These hydroxyquinolines are obtained in a conventional manner, for example by condensing a corresponding aniline with a β-ketoester in accordance with equations (1) and (2), as described in German Pat. No. 455,387.

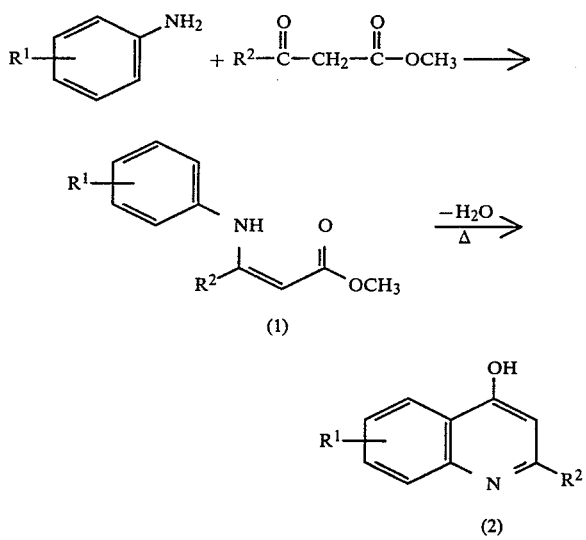

The 4-hydroxyquinolines, or the 4-alkoxyquinolines and 4-benzyloxyquinolines obtained by alkylation and aralkylation respectively can be oxidized to the corresponding compounds of the formulae Ia and Ib by means of per-acids or $H_2O_2$ in acetic acid solution, preferably by means of peracetic acid, perphthalic acid or m-chloroperbenzoic acid, with or without molybdic acid or tungstic acid as the catalyst. In the case of the oxidation of the 4-hydroxyquinolines, the 4-hydroxyl group is advantageously protected by esterification with acetic acid, a chlorocarbonic acid ester or benzoic acid. After oxidation has been effected, the protective group can easily be removed by stirring the compound with dilute sodium hydroxide or potassium hydroxide solution at from 0° to 60° C., preferably from 10° to 30° C. The product is then precipitated, in good purity, by acidification.

A further method of preparation is based on that of Gabriel and Gerhard in Chem. Ber. 54 (1921), 1071 and 1072, who obtained 4-hydroxyquinaldine-N-oxide by reduction of o-nitrobenzoylacetone.

The novel compounds of the formula Ia, where $R^3$ is not H, are obtained from the intermediate ($R^3$=H) by alkylation or aralkylation with a dialkyl sulfate, dialkyl sulfite, alkyl halide or benzyl halide. Suitable solvents are polar solvents, eg. tetrahydrofuran, dioxane, ether or dimethylformamide, in the presence or absence of a base and of up to 50% of water.

Specific examples are 4-hydroxyquinaldine-N-oxide, 6-methyl-4-hydroxyquinaldine-N-oxide, 6-ethoxy-4-hydroxyquinaldine-N-oxide, 6-chloro-4-hydroxyquinaldine-N-oxide, 8-methyl-4-hydroxyquinaldine-N-oxide, N-methoxy-quinald-4-one, 6-methyl-N-methoxy-quinald-4-one, 4-methoxy-quinaldine-N-oxide, 6-ethoxy-4-methoxy-quinaldine-N-oxide, 4-benzyloxy-quinaldine-N-oxide, 6-chloro-4-methoxy-quinaldine-N-oxide and 2-butyl-4-hydroxyquinoline-N-oxide.

EXAMPLE 1

80 g (0.5 mole) of 4-hydroxyquinaldine are converted into the Na salt by means of 27 g (0.5 mole) of $NaOCH_3$ in 400 ml of dry methanol. After removal of the methanol by evaporation under reduced pressure from a waterpump, the dry Na salt is suspended in 700 ml of dry toluene, and 54 g (0.5 mole) of ethyl chloroformate are added slowly at 80° C. After 2 hours, the solvent is distilled off under reduced pressure from a waterpump and the residue is stirred with 600 ml of methylene chloride for 30 minutes and then filtered off.

82.5 g (0.5 mole) of 85% strength m-chloroperbenzoic acid are added, a little at a time, to the filtrate at 15° C. After one hour, the mixture is extracted by shaking with cold dilute sodium carbonate solution and with water, and the organic phase is dried and concentrated under reduced pressure from a waterpump. The residue is taken up in 200 ml of 50% strength ethanol and a solution of 16 g of KOH in 200 ml of 50% strength ethanol is added at room temperature. After 30 minutes, the mixture is concentrated to half its volume and the product is precipitated by acidifying to pH 4 with 2N HCl. 47–60 g of crude product are obtained. This can, if desired, be recrystallized from methanol to give pure 4-hydroxyquinaldine-N-oxide. Melting point 248°–250° C.

EXAMPLE 2

14 g (0.08 mole) of 4-hydroxyquinaldine-N-oxide are suspended in 400 ml of dioxane, and 4.8 g (0.12 mole) of NaOH in 80 ml of $H_2O$ are added. The mixture is stirred at 50° C., and 13.2 g (0.116 mole) of dimethyl sulfate in 80 ml of dioxane are added dropwise. After 2 hours, the solution is concentrated under reduced pressure from a waterpump, the residue is taken up in 20 ml of water and the mixture is acidified to pH 1 with concentrated HCl. Filtration and drying gives 14 g of a crude product, which can be recrystallized from water in the presence of active charcoal. Yield 6–8 g of N-methoxy-quinald-4-one. Melting point 186°–188° C. (with decomposition).

EXAMPLE 3

31 g of 4-methoxyquinaldine (prepared from 4-hydroxyquinaldine by the method of M. Maurin, A. Ch. 4 [11] (1935), 301 and 335) are taken up in 80 ml of chloroform at room temperature, and 42 g of 85% strength m-chloroperbenzoic acid are added a little at a time, with stirring. The mixture is heated at 40° C. for 2 hours and is then cooled to 20° C. and brought to pH 6–7 with about 9 g of NaOH in 50 ml of $H_2O$. The organic phase is separated off, dried with $Na_2SO_4$, filtered and concentrated. 34 g of crude product remain, and are recrystallized from toluene with addition of a small amount of solid KOH. 12 g of pure 4-methoxyquinaldine-N-oxide are obtained. Melting point 131°–132° C.

EXAMPLE 4

The compounds shown below are obtained by methods similar to those described in Examples 1–3.

TABLE 1

| Structure | Melting point [°C.] | Analysis | | | |
|---|---|---|---|---|---|
| 6-EtO, 2-CH₃, N-OH quinolin-4(1H)-one | 248–250 | C 65.74<br>65.7 | H 5.98<br>6.0 | N 6.39<br>6.4 | calc.<br>found |
| 8-CH₃, 2-CH₃, N-OH quinolin-4(1H)-one | 253–254 | C 69.83<br>70.0 | H 5.86<br>6.1 | N 7.40<br>7.7 | calc.<br>found |
| 2-CH₃, N-OCH₃ quinolin-4(1H)-one | 186–188 (decomposition) | C 69.84<br>70.1 | H 5.86<br>6.0 | N 7.40<br>7.5 | calc.<br>found |
| 6-EtO, 2-CH₃, N-OCH₃ quinolin-4(1H)-one | No analytical data; very hygroscopic | | | | |
| 6-CH₃, 2-CH₃, N-OH quinolin-4(1H)-one | 248–252 | C 69.83<br>70.3 | H 5.86<br>5.9 | N 7.40<br>7.6 | calc.<br>found |
| 6-Cl, 2-CH₃, N-OH quinolin-4(1H)-one | 265–267 (decomposition) | C 57.28<br>57.1 | H 3.82<br>3.8 | N 6.68<br>6.7 | calc.<br>found |
| 6-Cl, 2-CH₃, N-OCH₃ quinolin-4(1H)-one | 128–133 | C 59.06<br>59.3 | H 4.47<br>4.7 | N 6.26<br>6.3 | calc.<br>found |

EXAMPLE 5

Feed additives containing a compound of the formula Ia or Ib as the active ingredient may be formulated as follows:

A 10% strength concentrate is prepared by milling 10 g of active ingredient of the formula Ia or Ib and 90 g of corn starch; this concentrate is then diluted to a 1% strength premix by further milling with 900 g of wheat grits bran.

On mixing 10 g of the premix with 990 g of a commercial standard feed for pigs, poultry or ruminants, a feed containing 100 ppm of active ingredient is obtained.

EXAMPLE 6

A premix of the following composition is prepared for young pigs:

| Constituents | Amount |
| --- | --- |
| Vitamin A | 1,200,000 IU |
| Vitamin D₃ | 300,000 IU |
| Vitamin E | 2,000 IU |
| Vitamin B₂ | 600 mg |
| Vitamin B₃ | 2,000 mg |
| Vitamin B₁₂ | 5 mg |
| Nicotinic acid (niacin) | 3,000 mg |
| Choline chloride | 40,000 mg |
| N—Methoxy-quinald-4-one (from Example 2) | 1,000 mg |
| Butylhydroxytoluene (antioxidant) | 30,000 mg |

| Trace elements | |
| --- | --- |
| Manganese | 6,000 mg |
| Iron | 10,000 mg |
| Zinc | 15,000 mg |
| Copper | 30,000 mg |
| Iodine | 100 mg |
| Doubly milled bran to make up to | 1,000 mg |

0.5 kg of this vitamin and trace element premix is added to 100 kg of base feed.

EXAMPLE 7

0.5 kg of the premix prepared in Example 6 is added to a base feed of the following composition:

| Constituent | Amount |
| --- | --- |
| Indian corn | 25.0 kg |
| Wheat | 34.0 kg |
| Extracted soybean | 18.0 kg |
| Milk powder | 9.9 kg |
| Fishmeal | 4.0 kg |
| Fodder yeast | 2.0 kg |
| Fat powder | 3.4 kg |
| Mineral premix (dicalcium phosphate/monocalcium phosphate/calcium carbonate = 55/40/5) | 1.8 kg |
| Feed lime | 1.0 kg |
| Feed-grade sodium chloride | 0.4 kg |
| Premix of Example 6 | 0.5 kg |
| Total weight | 100.0 kg |

The resulting young pig feed contains 5 ppm=0.0005% by weight of active ingredient.

EXAMPLE 8

A feeding test was carried out on rats to illustrate the effectiveness of the novel feeds in respect of improvement of growth and of feed utilization:

The test animals, male Sprague-Dawley rats (from Jautz, Kisslegg) were kept in groups of three in polycarbonate cages and were fed with a commercial test animal feed (from Eggersmann, Rinteln). The feed and water were available ad libitum. The results are shown in Table 2.

TABLE 2

| Substance | Concentration in feed | No. of animals | Body weight per animal Day 0 | Body weight per animal Day 21 | Weight increase in % of the control | Feed utilization |
| --- | --- | --- | --- | --- | --- | --- |
| Control | — | 18 | 74.9 ± 2.9 | 209 ± 12.2 | 100 | 2.67 |
| 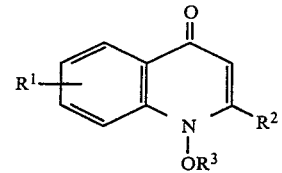 | 10 ppm | 9 | 74.8 ± 2.9 | 215.6 ± 12.3 | 104.6 | 2.59 |
| 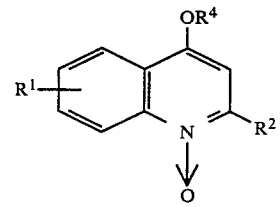 | 5 ppm | 9 | 74.8 ± 2.1 | 219.6 ± 13.9 | 107.6 | 2.55 |

We claim:

1. A growth-promoting feed or drink which in addition to a conventional feed premix, feed concentrate or feed, or water, as the main constituent contains from 0.5 to 500 ppm of a compound of the formula Ia or Ib Ia Ib where $R^1$ is hydrogen, low molecular weight alkyl or alkoxy, or halogen, $R^2$ is low molecular weight alkyl and $R^3$ and $R^4$ are hydrogen, a low molecular weight aliphatic radical or a benzyl radical.

2. A feed or drink as set forth in claim 1, which contains 4-hydroxyquinaldine-N-oxide, 6-chloro-4-hydroxyquinaldine-N-oxide, 6-chloro-N-methoxyquinald-4-one, 8-methyl-N-methoxy-quinald-4-one, 4-methoxyquinaldine-N-oxide, 6-ethoxy-4-methoxyquinaldine-N-oxide, or 2-butyl-4-hydroxyquinoline-N-oxide.

3. A compound of the formula IVa or IVb
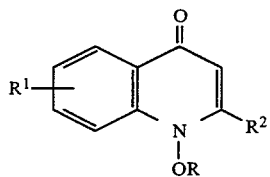
IVa
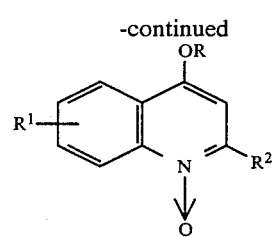
IVb
where $R^1$ is hydrogen, low molecular weight alkyl or alkoxy or halogen, $R^2$ is low molecular weight alkyl and R is methyl, ethyl or benzyl.
* * * * *